United States Patent [19]

Hellberg et al.

[11] Patent Number: 5,686,450
[45] Date of Patent: Nov. 11, 1997

[54] USE OF N,N'-BIS(MERCAPTOACETYL) HYDRAZINE DERIVATIVES AS ANTICATARACT AGENTS

[75] Inventors: Mark R. Hellberg, Arlington; William H. Garner, Southlake; Jaime E. Dickerson, Jr., Fort Worth, all of Tex.; Marjorie F. Lou, Lincoln, Nebr.

[73] Assignee: Alcon Laboratories, Inc., Fort Worth, Tex.

[21] Appl. No.: 472,452

[22] Filed: Jun. 7, 1995

[51] Int. Cl.$^6$ .................................................. A61K 31/54
[52] U.S. Cl. ........................... 514/222.5; 514/912
[58] Field of Search ........................... 514/222.5, 912

[56] References Cited

FOREIGN PATENT DOCUMENTS

| 0 499 882 A | 8/1992 | European Pat. Off. |
| 0 397 437 A | 2/1994 | European Pat. Off. |
| WO 94/03167 | 2/1994 | WIPO |

OTHER PUBLICATIONS

Atkinson, E. R., "Potential Antiradiation Drugs", *Journal Of Medicinal Chemistry*, vol. 8, No. 1, pp. 29–33 (1965).
Derwent Publications Ltd., London, GB; AN 83–702291, XP002013383 & JP,A,58 088 350 (Santen Seiyaku), 26, May 1983.
Lamoureaux, G., et al., "Synthesis Of Dithiols As Reducing Agents For Disulfides In Neutral Aqueous Solution And Comparison Of Reduction Potentials", *The Journal Of Organic Chemistry*, vol. 58, No. 3, pp. 633–641 (1993).
Setogawa, T., et al., "Preventive Effect Of SA3443, A Novel Cyclic Disulfide, On Glucocorticoid–Induced Cataract Formation Of Developing Chick Embyro", *Experimental Eye Research*, vol. 58, No. 6, pp. 689–695 (1994).

*Primary Examiner*—Zohreh Fay
*Attorney, Agent, or Firm*—Michael C. Mayo

[57] ABSTRACT

Compositions containing certain sulfur containing compounds and methods of use in the treatment and prevention of cataracts is disclosed.

6 Claims, No Drawings

USE OF N,N'-BIS(MERCAPTOACETYL) HYDRAZINE DERIVATIVES AS ANTICATARACT AGENTS

BACKGROUND OF THE INVENTION

The present invention relates to the field of ophthalmology. In particular, the invention is directed to compounds used to prevent or limit the progression of cataracts.

The lens is made up of a concentric layer of cells somewhat like the regularity of layers in an onion. Lens transparency is the result of a uniform structure of the cell's cytoplasm, which exists in an ordered, homogenous state (*Applied Optics*, volume 10, pages 459–473 (1971)). These cells contain primarily the crystallin proteins. When these protein are modified by oxidative stress, conformational changes and aggregates result, which in turn disrupts the protein lattice and damages the cell This cellular damage leads to a further disruption of the regular layers of cells, resulting in opacities, or cataracts of the lens.

Crystallins, which occur in $\alpha$, $\beta$, $\gamma$ and other subtypes, are proteins containing numerous sulfhydryl groups. These sulfhydryl groups can be oxidized to form disulfide groups. When this occurs, the protein is conformationally altered and/or cross-linked via disulfide linkages with other proteins or molecules containing sulfhydryl groups. This oxidation has been implicated in the formation of cataracts (*Investigative Ophthalmology and Visual Science*, volume 25(2), pages 30–146 (1984)). Dickerson has reported that certain mixed disulfides are formed including: protein-$\gamma$-glutamylcysteine (PSS$\gamma$-GluCys), protein-cysteine (PSSC), and protein-glutathione (PSSG). (*Biochimica et Biophysica Acta*, volume 1157, pages 141–146 (1993). Further, it has been reported that elevated levels of these mixed disulfides are present in cataractous lenses, and this finding has also been demonstrated in vitro, with lenses exposed to oxidative stress (*Experimental Eye Research*, volume 50, pages 819–826 (1990)).

Certain endogenous biomolecules can help reduce oxidative stress, and thus inhibit protein oxidation. Reduced glutathione (GSH) and other thiol containing molecules act at least indirectly as oxygen free radical scavengers, due to their easily oxidizable sulfhydryl groups, and hence act as sulfhydryl antioxidants in normal lenses. Glutathione reductase regenerates GSH from its disulfide oxidized form, glutathione-S-S-glutathione (GSSG), and acts as a sulfhydryl buffering system, continually controlling the sulfhydryl/disulfide balance in the cell. GSH exists in great excess of its GSSG oxidized counterpart in the cellular cytoplasm, thus creating a strong potential for cytosolic proteins to exist in a sulfhydryl-reduced, non-crosslinked state. Deficiencies of GSH have been observed in cataractious lenses (*Biochimica et Biophysica Acta*, Volume 1138, pages 11–19 (1992)). This deficiency leads to a reduced ability of the cell to repair damage associated with oxidative stress.

Antioxidant therapy has been proposed to ameliorate the destructive effects of oxidation resulting in the formation of cataracts (*American Journal of Clinical Nutrition*, Volume 53, pages 335S–345S (1991) and *American Journal of Clinical Nutrition*, Volume 53, pages 352S–355S (1991)). Such proposed therapy has included the systemic administration of the naturally occurring Vitamins C and E as well as $\beta$-carotene. The use of phenolic antioxidants, such as probucol, to inhibit the development of cataracts, has been disclosed in U.S. Pat. No. 5,061,734 (Mao et al.). While these studies and patent suggest the viability of antioxidant therapy, they do not address the use of a glutathione mimic to inhibit the formation and progression of cataracts.

As GSH is a disulfide reducing agent, it is believed that the administration of other sulfhaydryl compounds to the GSH-depleted, cataract-susceptible cells would bolster the reducing capability of the lens cells. The use of disulfhydryl compounds has been proposed in PCT Application No. WO 94/03167, and Free Radical in Biology and Medicine, volume 18, pages 823–829 (1995). These compounds contain an amide as well as a carboxylic acid moiety. The compounds of the present invention are hydrazine sulfhydryls, thioesters and disulfides. U.S. Pat. No. 5,399,573 (Garner) discloses cyclized cysteine pro-drags for use in cataract therapy. The compounds of the present invention are disulfides or dithioesters which can participate in disulfide exchange, acting in a catalytic manner as a glutathione mimetic.

Certain disulfide and dithioester compounds of the present invention have been previously prepared (*Journal of Organic Chemistry*, volume 56, pages 2332–2337 (1991)). These compounds have been reported to be reagents that reduce disulfide bonds in proteins.

Currently, there is no accepted, non-surgical therapy for the treatment of cataracts. The compounds and methods of the present invention provide an alternative non-surgical approach to cataract surgery. This new therapy provides the advantages of a non-invasive, less-costly treatment for cataract prevention and amelioration.

SUMMARY OF THE INVENTION

The present invention is directed to compositions and methods for treating or delaying the onset of cataracts in humans through the administration of the compounds described below.

DETAILED DESCRIPTION OF THE INVENTION

The present invention is based on the finding that certain disulfhydryl containing compounds possess antioxidant and disulfide reducing efficacy. The present invention is also based on the finding that these compounds possess membrane permeability and thus would be bioavailable for the treatment of cataracts.

The compounds used in the present invention have the following formula (I):

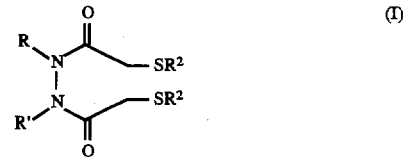

wherein,

R and R' are independently H, $C_{1-10}$ alkyl, (un)substituted aryl, (un)substituted heterocycle, or may form a ring of formula (II):

wherein n is 1–3;

R2 is

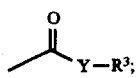

Y is NH or CH$_2$;

R$^3$ is H, C$_{1-10}$ alkyl, (un)substituted aryl, (un)substituted heterocycle; and provided that R$^2$ may be absent, wherein the two sulfur atoms form a disulfide bond of formula (III):

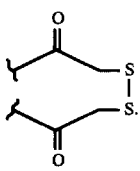

Particularly preferred are the compounds:

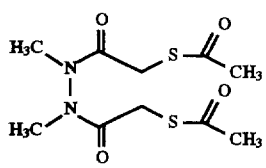

The compounds of formula (I) act to reduce mixed disulfide formation, as described above, and further aid in stabilizing or increasing the amount of GSH in the cytosol of lens cell. The compounds of formula (I) are administered in a therapeutically effective amount to reduce and/or inhibit cataract formation in the mammalian lens. As used herein, the term "therapeutically effective amount" is that amount of a compound of formula (I) which reduces, inhibits and/or causes delay in the onset of cataracts in a mammal having a predisposition, propensity, likelihood or possibility of forming cataracts. A given therapeutic concentration may vary from individual to individual, due to physiological differences, mammal to mammal, or condition to condition, due to severity and exposure to cataractogenic factors. As such, no single therapeutic concentration can be determined. Clinicians skilled in the art will determine the amount based on clinical examinations, studies and experimentations.

The compounds of present invention can be prepared by literature methods analogous to those used to prepare the known compounds (1) and (2) (*Journal of Organic Chemistry*, volume 56, pages 2332–2337 (1991)). This route is outlined in Scheme 1 below:

Scheme 1

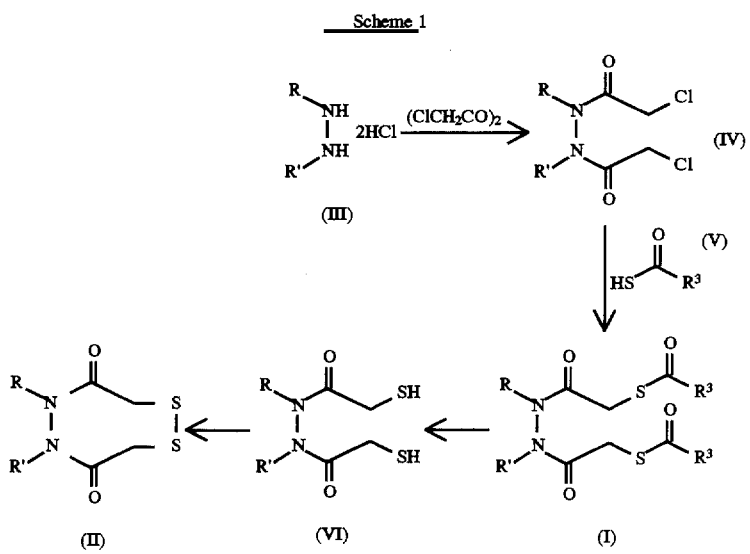

The hydrazine derivative (III), which is commercially available or which may be prepared by methods known to those skilled in the art, is reacted with chloroacetic anhydride to provide the bis acyl hydrazine derivative (IV). This compound is reacted with the appropriate thiolcarboxylic acid (V) in the presence of a base such as triethylamine to give the bis thioester (I). Cleavage of the thioester provides the disulfhydryl (VI) and mild oxidation of (VI) provides the disulfide (II).

The compounds of the present invention are further illustrated by the following synthesis examples:

EXAMPLE 1

N,N'-Diphenyl-N,N'-bis[(acetylthio)acetyl]hydrazine (Compound 3)

In order to make the title compound, the intermediate, N,N'-Diphenyl-N,N'-bis(chloroacetyl)hydrazine (Intermediate 1), is first synthesized:

N,N'-diphenylhydrazine (Aldrich, Milwaukee, Wis.) (76.3 mmol) and chloroacetic anhydride (Aldrich, Milwaukee, Wis.) (420 mmol) are combined and warmed. The resulting mixture is cooled to room temperature and is cautiously added to ice water (1.2 L). Methylene chloride (400 mL) is added, and the resulting mixture is adjusted to pH 7 by the addition of 50% sodium hydroxide. The methylene chloride layer is separated, washed with brine, dried (MgSO$_4$) and concentrated under reduced pressure to give the crude product which was purified by standard methods.

To a solution of N,N'-diphenyl-N,N'-bis(chloroacetyl) hydrazine (6.10 mmol) in methylene chloride (100 mL) in an ice bath, is added thiolacetic acid (Aldrich, Milwaukee, Wis.) (18.2 mmol) followed by triethylamine (17.43 mmol). The solution is stirred in an ice bath. The reaction mixture is washed with water, cold 10% aqueous $NaHCO_3$ solution and brine. The resulting solution is dried ($MgSO_4$), and concentrated under reduced pressure to give the crude product. Purification by standard methods afford the product.

EXAMPLE 2

Hexahydro N,N'-diphenyl-4,7-dioxo-1,2-dithia-5,6-diazocine (Compound 4)

In order to make the title compound, the intermediate, N,N'-Diphenyl-N,N'-bis(mercaptoacetyl) hydrazine (Intermediate 2), is first synthesized:

To a solution of N,N'-Diphenyl-N,N'-bis[(acetylthio)acetyl]hydrazine (3.42 mmol) in methanol (20 mL) is added concentrated HCl (0.2 mL of a 37% aqueous solution), and the resultant solution is then stirred at room temperature. The reaction mixture was concentrated at reduced pressure to provide the crude product which was used without further purification.

To a solution of crude N,N'-diphenyl-N,N'-bis (mercaptoacetyl) hydrazine (5.2 mmol), in ethyl acetate (150 mL) in an ice bath, is added a cold $KHCO_3$ solution (50 mL of a 10% aqueous solution). A solution of iodine (5.2 mmol) in ethyl acetate is then added dropwise with stirring until the reaction mixture turned brown. An aqueous solution of sodium thiosulfate is added to quench the excess iodine. The ethyl acetate layer is separated, and the aqueous layer is extracted with ethyl acetate. The combined ethyl acetate extracts are dried ($Na_2SO_4$) and concentrated under reduced pressure. The crude product is purified using standard procedures.

EXAMPLE 3

N,N'-Dimethyl-N,N'-bis[(pivalolylthio)acetyl] hydrazine (Compound 5)

To a solution of N,N'-dimethyl-N,N'-bis(chloroacetyl) hydrazine (*Journal of Organic Chemistry*, volume 56, pages 2332–2337 (1991)) (6.1 mmol), in methylene chloride, is added thiolpivalic acid (Aldrich, Milwaukee, Wis.) (18.2 mmol) followed by triethylamine (17.3 mmol). The solution is stirred in an ice bath. The solution is washed with water, cold 10% aqueous $NaHCO_3$ solution, and brine. The resulting solution is dried ($MgSO_4$) and concentrated under reduced pressure. The crude product is purified using standard procedures.

EXAMPLE 4

N-Butyl,N'-ethyl-N,N'-bis[(acetylthio)acetyl] hydrazine (Compound 6)

Following the procedure for the preparation of Compound 3, the title compound is prepared by substituting N,N-butylamino ethylamine (Lancaster, Windham, N.H.) for N,N'-diphenylhydrazine.

EXAMPLE 5

Hexahydro N-butyl,N'-ethyl-4,7-dioxo-1,2-dithia-5,6-diazocine (Compound 7)

In order to make the title compound, the intermediate, N-Butyl,N'-ethyl-N,N'-bis(mercaptoacetyl) hydrazine (Intermediate 3), is first synthesized:

Following the procedure for the preparation of Intermediate 2, N-Butyl,N'-ethyl-N,N'-bis(mercaptoacetyl) hydrazine (Intermediate 3) is prepared by substituting N-butyl, N'-ethyl-N,N'-bis[(acetylthio)acetyl]hydrazine for N,N'-Diphenyl-N,N'-bis[(acetylthio)acetyl]hydrazine.

Following the procedure for the preparation of Compound 4, the title compound is prepared by substituting N-butyl, N'-ethyl-N,N'-bis(mercaptoacetyl) hydrazine (Intermediate 3) for N,N'-diphenyl-N,N'-bis(mercaptoacetyl) hydrazine.

The compounds of formula (I) may be contained in various types of pharmaceutical compositions, in accordance with formulation techniques known to those skilled in the art. For example, the compounds may be included in tablets, capsules, solutions, suspensions and other dosage forms adapted for oral administration; and solutions and suspensions adapted for parenteral and topical use.

The present invention is particularly directed to the provision of compositions adapted for topical treatment of ophthalmic tissues. The ophthalmic compositions of the present invention will include one or more compounds of formula (I) and a pharmaceutically acceptable vehicle for said compound(s). Various types of vehicles may be utilized. The vehicles will generally be aqueous in nature. Aqueous solutions are generally preferred, based on ease of formulation, as well as patients' ability to easily administer such compositions by means of instilling one to two drops of the solutions in the affected eyes. However, the compounds of formula (I) may also be readily incorporated into other types of compositions, such as suspensions, viscous or semi-viscous gels or other types of solid or semi-solid compositions. Suspensions may be preferred for compounds of formula (I) which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium 1, or other agents known to those skilled in the art. Such preservatives are typically employed at a level of from 0.001 to 1.0 percent by weight, based on the total weight of the composition (wt. %).

Some of the compounds of formula (I) may have limited solubility in water and therefore may require a surfactant or other appropriate co-solvent in the composition. Such co-solvents include: polyethoxylated castor oils, Polysorbate 20, 60 and 80; Pluronic® F-68, F-84 and P-103 (BASF Corp., Parsippany N.J., USA); cyclodextrin; or other agents known to those skilled in the art. Such co-solvents are typically employed at a level of from 0.01 to 2 wt. %.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from 0.01 to 2 wt. %.

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, the compounds of formula (I) are used to prevent or reduce cataracts at the cellular level. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The use of physiologically balanced irrigating solutions as pharmaceutical vehicles for the compounds of formula (I) is preferred when the compounds are administered intraocularly. As utilized herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a buffer to maintain the pH of the solution at or near physiological levels. Various solutions of this type are known (e.g., Lactated Ringers Solution). BSS® Sterile Irrigating Solution and BSS Plus® Sterile Intraocular is Irrigating Solution (Alcon Laboratories, Inc., Fort Worth, Tex., USA) are examples of physiologically balanced intraocular irrigating solutions. The Latter type of solution is described in U.S. Pat. No. 4,550,022 (Garabedian, et at), the entire contents of which are hereby incorporated in the present specification by reference.

The doses utilized for any of the above-described purposes of topical ocular or systemic administration will generally be from about 0.01 to about 100 milligrams per kilogram of body weight (mg/kg), administered one to four times per day.

The compositions of the present invention are further illustrated by the following formulation examples. The ingredient "Compound" denotes a compound of the present invention.

EXAMPLE 6

A typical eye drop formulation for topical administration may contain the following:

| A typical eye drop formulation for topical administration may contain the following: | | |
|---|---|---|
| Ingredient | Amount (wt %) | Purpose |
| Compound | 0.1 | active ingredient |
| Polyvinyl alcohol, USP | 1.4 | excipent |
| Mono sodium phosphate (monohydrate), USP | 0.05 | buffering agent |
| Dibasic sodium phosphate (Anhydrous), 'USP | 0.15 | buffering agent |
| Sodium chloride, USP | 0.5 | tonicity agent |
| Disodium EDTA (edetate disodium), USP | 0.01 | preservative |
| Polysorbate 80, NF | 0.05 | surfactant |
| Benzalkonium chloride solution, NF | 0.01 + 5 excess | preservative |
| Sodium hydroxide, NF | q.s. | pH adjustment |

| A typical eye drop formulation for topical administration may contain the following: | | |
|---|---|---|
| Ingredient | Amount (wt %) | Purpose |
| Hydrochloric acid, NF | q.s. | pH adjustment |
| Water for injection, USP | q.s. | vehicle |

EXAMPLE 7

A typical eye drop formulation for topical administration may contain the following:

| A typical eye drop formulation for topical administration may contain the following: | | |
|---|---|---|
| Ingredient | Amount (wt %) | Purpose |
| Compound | 0.1 | active ingredient |
| Sodium chloride, USP | 0.7 | tonicity |
| Boric acid, USP | 0.4 | preservative |
| Methyl p-hydroxybenzoate, USP | 0.002 | preservative |
| Chlorobutanol, USP | 0.03 | Preservative |
| Sodium hydroxide, NF | q.s. | pH adjustment |
| Hydrochloric acid, NF | q.s. | pH adjustment |
| Water for injection, USP | q.s. | vehicle |

The compounds of the present invention are further illustrated by the following biological studies example:

EXAMPLE 8

The efficacy of compounds of the present invention to inhibit $H_2O_2$-mediated mixed disulfide formation and GSH depletion in a cultured rat lens model was ascertained. Rat lenses were excised from rats, and cultured in modified TC-199 media as described in *Experimental Eye Research*, 41:67–79 (1985). Cultured rat lenses were incubated at 37° C. for 20.5 hours: 1) without $H_2O_2$ or Compound 1, above (Control); 2) with only $H_2O_2$ (0.5 mM); or 3) with both $H_2O_2$ and Compound 1 (0.1 mM). GSH and mixed disulfide measurements were obtained by chromatography, using the methods described in *Experimental Eye Research*, 42:607–616 (1986).

The data are reported in Table I below:

TABLE I

| GSH and Mixed Disulfide Levels in Cultured Rat Lenses | | | |
|---|---|---|---|
|  | Control | $H_2O_2$ | $H_2O_2$ + Compound 1 |
| GSH (mmol/gram wet weight) | 3.96 ± 0.27 | 0.38 ± 0.13 (−90%) | 1.09 ± 0.26 (−72%) |
| PSSC (mmol/gram dry weight) | 0.51 ± 0.05 | 0.90 ± 0.19 (+176%) | 0.70 ± 0.30 (+137%) |
| PSSG (mmol/gram dry weight) | 0.13 ± 0.11 | 3.82 ± 0.23 (30 ×) | 3.00 ± 0.82 (23 ×) |

Mixed disulfide (PSSC and PSSG) formation increased in cultured lenses treated with $H_2O_2$ by about 75% for PSSC and 30-fold for PSSG over control levels. Compound 1 inhibited both PSSC and PSSG formations by 39 and 24%, respectively, over the control insult. The GSH concentration was depleted to only 10% of control after the $H_2O_2$ insult. Treatment with Compound 1 ameliorated some of this GSH depletion, maintaining about 30% of the GSH as compared to control levels.

The invention in its broader aspects is not limited to the specific details shown and described above. Departures may be made from such details within the scope of the accompanying claims without departing from the principles of the invention and without sacrificing its advantages.

What is claimed is:

1. A method of treating and/or delaying the onset of cataract in mammals comprising administering to the mammal a composition having a therapeutically effective amount of a compound of formula (III):

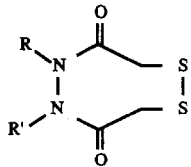
(III)

wherein,

R and R' are independently H, $C_{2-10}$ alkyl, (un)substituted aryl, (un)substituted heterocycle, or may form a ring of formula (II):

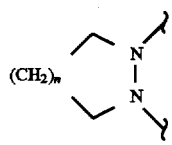
(II)

wherein n is 1–3.

2. A method according to claim 1 wherein R and R' are independently methyl, ethyl, butyl or benzyl.

3. A method according to claim 1 wherein the compound is selected from the group consisting of:

Hexahydro N,N'dimethyl-4,7-dioxo-1,2-dithia-5,6-diazocine;

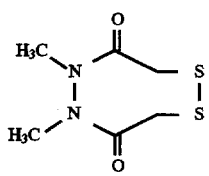

Hexahydro N,N'-dimethyl-4,7-dioxo-1,2-dithia-5,6-diazocine;

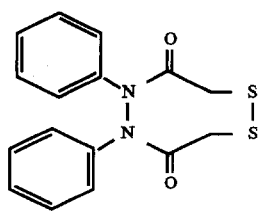

Hexahydro N,N'-diphenyl-4,7-dioxo-1,2-diathia-5,6-diazocine; and

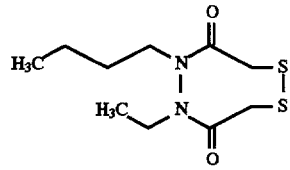

4. A composition for treating and/or delaying the onset of cataracts in mammals comprising a therapeutically effective amount of a compound of formula (III):

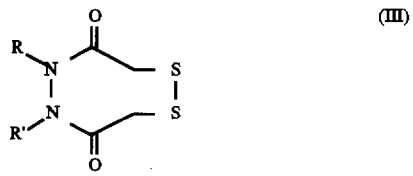
(III)

wherein,

R and R' are independently H, $C_{2-10}$ alkyl, (un)substituted aryl, (un)substituted heterocycle, or may form a ring of formula (II):

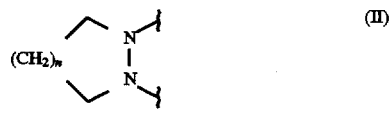
(II)

wherein n is 1–3.

5. A composition according to claim 4 wherein R and R' are independently methyl, ethyl, butyl or benzyl.

6. A composition according to claim 4 wherein the compound is selected from the group consisting of:

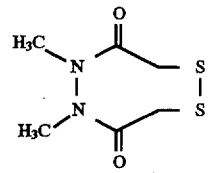

Hexahydro N,N'-dimethyl-4,7-dioxo-1,2-dithia-5,6-diazocine;

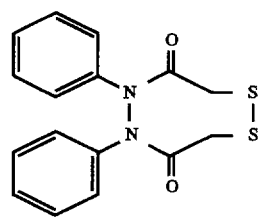

Hexahydro N,N'-diphethyl-4,7-dioxo-1,2-diathia-5,6-diazocine; and

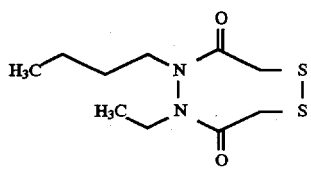

Hexahydro N-butyl, N'-ethyl-4,7-dioxo-1,2-dithia-5,6-diazocine.

* * * * *